United States Patent [19]

Gamm

[11] Patent Number: 4,632,106

[45] Date of Patent: Dec. 30, 1986

[54] STRETCHABLE TUBULAR BRACE FOR KNEE OR ELBOW AND METHOD OF CONSTRUCTION

[75] Inventor: Paul B. Gamm, Cincinnati, Ohio

[73] Assignee: Jung Corporation, Ohio

[21] Appl. No.: 823,311

[22] Filed: Jan. 28, 1986

[51] Int. Cl.⁴ .............................................. A61F 13/00
[52] U.S. Cl. ..................................................... 128/165
[58] Field of Search ......................................... 128/165

[56] References Cited

U.S. PATENT DOCUMENTS

| | | | |
|---|---|---|---|
| 663,749 | 12/1900 | Gorse | 128/165 |
| 1,853,903 | 4/1932 | Kendrick | 128/165 |
| 4,269,181 | 5/1981 | Delannoy | 128/165 |

Primary Examiner—Gregory E. McNeill
Attorney, Agent, or Firm—Wood, Herron & Evans

[57] ABSTRACT

A tubular brace constructed so that no seam overlies the fold line of the surface skin behind the user's knee, or on top of the user's elbow, when the brace is being worn, thereby minimizing abrasive discomfort at those surface skin fold areas. Specifically, a first rear surface stitch line is positioned above the surface skin fold line at the knee or elbow joint, and a second rear surface stitch line is positioned below that surface skin fold line, these stitch lines being generally transverse to the brace's longitudinal axis, and these stitch lines cooperating with a generally longitudinal stitch line that extends between the brace's top and bottom edges.

10 Claims, 8 Drawing Figures

STRETCHABLE TUBULAR BRACE FOR KNEE OR ELBOW AND METHOD OF CONSTRUCTION

This invention relates to braces. More particularly, this invention relates to an elastic brace particularly adapted for use on a person's knee or person's elbow, and to a method of constructing same from a one piece blank of stretchable material.

Tubular or sleeve like braces are very well known to the prior art. These elastic braces have been used for many years as knee braces or elbow braces. Such braces provide some degree of support to the joint of the person that wears the brace while that person is engaged in an activity that requires or results in significant exercise.

In recent years it has become known to make these tubular knee or elbow braces out of a laminate material that includes a foam rubber sheet as the primary substrate in configuration with a stretchable fabric on each surface of that substrate to provide the laminate's outer faces. This type foam rubber tubular brace has certain advantages in that it retains body heat, and provides a degree of compression and/or support for the knee or elbow joint, and thereby helps reduce strain or injury to that joint. To construct a tubular brace from the foam rubber laminate the laminate sheet must be cut to the desired configuration and sewn together from the flat piece state into the finished tubular state. And the requires seams or bindings in certain surface areas of the brace. With prior art braces of this type, such seams or bindings have been located on the inside surface area of the brace, i.e., on a knee brace the brace's inside surface covering the wearer's skin area in back of the knee joint, and on an elbow brace the brace's inside surface covering the wearer's skin area on top of the elbow joint. With these prior art braces the seams or bindings generally extend transverse to the longitudinal axis of the brace in that area where the wearer's skin flexes most, i.e., the fold line area of the wearer's skin. And interaction of the brace's seams with the skin surface fold line while the brace is being worn can cause significant irritation to the wearer's skin in that area in back of the knee joint or on top of the elbow joint. In other words, the construction methods of tubular braces of an elastic foam rubber laminate, and the braces that result therefrom, as heretofore known, are such that the seams or bindings required to sew the brace into tubular configuration from a one piece material blank provide irritation to the skin on the back skin surface of the wearer's knee in the case of a knee brace, or to the inside skin surface of the wearer's arm in the case of an elbow brace.

Accordingly, it has been the primary objective of this invention to provide an improved elastic tubular brace (and construction method therefor) of the type adapted for use on a wearer's knee or wearer's elbow in which the seams or bindings of the brace are located so that irritation to the wearer's skin on the back of the wearer's knee in the case of a knee brace, and on the top surface of a wearer's elbow in the case of an elbow brace, is minimized while the brace is being worn, and while the wearer engages in an activity that requires or results in significant exercise.

In this regard, the tubular brace of this invention constructed so that no seam overlies the fold line of the surface skin behind the user's knee, or on top of the user's elbow, when the brace is being worn, thereby minimizing abrasive discomfort at those surface skin fold areas. Specifically a first rear surface stitch line is positioned above the surface skin fold line at the knee or elbow joint, and a second rear surface stitch line is positioned below that surface skin fold line, those stitch lines being generally transverse to the brace's longitudinal axis, and these stitch lines cooperating with a generally longitudinal stitch line that extends between the brace's top and bottom edges. In construction of this tubular brace, the initial step is to provide a one piece blank of stretchable material with two elongated eye shaped slits cut therein, those slits extending inwardly from one side edge thereof, and those slits being spaced one from the other so the fold line of the brace wearer's skin lies therebetween when the finally constructed brace is being worn. The edges of each slit are then sewn together to close the eye shaped openings, and the side edges of the blank are sewn together to form the tubular sleeve brace product.

Other objectives and advantages of this invention will be more apparent from the following detailed description taken in conjunction with the drawings in which.

Figure 1:
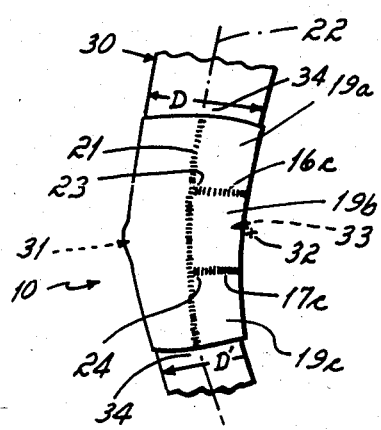
FIG. 1 is a side view illustrating one side of a knee brace in place on a wearer's leg, the brace being in accord with the principles of this invention.
Figure 2:
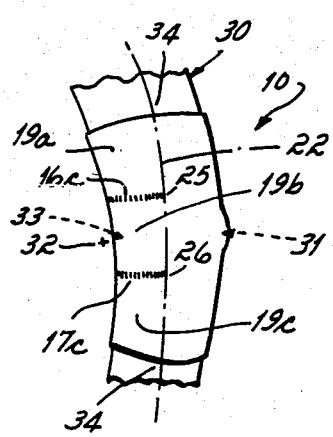
FIG. 2 is a side view of the other side of the brace shown in FIG. 1.
Figure 3:
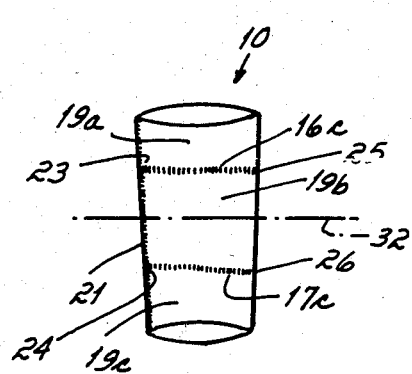
FIG. 3 is a rear view of the brace shown in FIG. 1.

A tubular or sleeve like brace 10 in accord with the principles of this invention, and in the form of a knee brace, is illustrated in FIGS. 1-3. A blank 11 from which the FIGS. 1-3 knee brace is fabricated, in accord with the construction method of this invention, is illustrated in FIG. 4.

Figure 4:
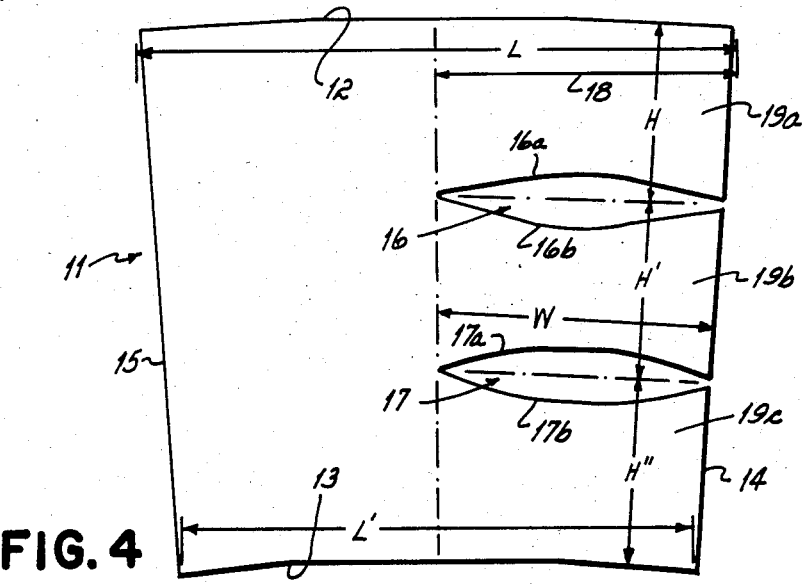
FIG. 4 is a top view of the blank from which the FIGS. 1-3 brace is fabricated.

The FIGS. 1-3 knee brace 10 is fabricated from a single unitary piece or blank 11 of elastic material, that blank having a geometry as illustrated in FIG. 4. The material itself is preferably a rubber foam laminate having a rubber (e.g., neoprene) foam core with a stretchable fabric bonded to each of the opposite faces thereof in order to create a sheet of material. This starter blank 11 is preferably sized and configured so that it includes a top edge 12 and a bottom edge 13, and opposed side edges 14, 15. The top edge 12 preferably is a slightly greater length L than the bottom L' of the bottom edge so as to establish a slightly larger diameter D for the brace 10 at its top edge than the diameter D' at its bottom edge when the brace is in final sleeve or tubular configuration. Note that one side edge 14 is slightly angled relative to the other side edge 15.

Most importantly relative to this invention, note that the blank 11 is provided with two elongated slits or openings 16, 17 of eye shaped configuration that are spaced relatively equally between the top 12 and bottom 13 edges of the blank. These slits or openings 16, 17 extend inwardly from one side edge 14 of the blank. These slits or openings 16, 17 are each of a length W approximately one-half the length L or L' of the blank, thereby locating those slits in only one longitudinal half section, i.e., the right hand half section 18, of the blank 11 as shown in FIG. 4. Further, the eye shaped slits 16, 17 subdivide that half section 18 of the blank which incorporates the slits into three subsections 19a, 19b, 19c of substantially equal height H, H', H", respectively, between top 12 and bottom 13 edges of the blank.

In construction of the brace 10 from the blank 11, the edges 16a, 16b and 17a, 17b of each eye shaped slit 16, 17 are sewn or bound together to eliminate the openings 16, 17 in the final brace structure, same being illustrated in FIGS. 1-3 by transverse binding lines 16c, 17c. Further, the two side edges 14, 15 of the blank 11 are sewn or bound together so as to establish the flat blank in a sleeve or tubular configuration, same being illustrated by longitudinal binding line 21, see FIG. 1.

The final knee brace 10 fabricated from the one piece blank 11 shown in FIG. 4 is, as earlier mentioned, illustrated in FIGS. 1-3. The knee brace 10 itself, as illustrated in the side view of FIG. 2, presents a generally curved longitudinal axis 22. Accordingly, when the knee brace 10 is installed on a wearer's leg 30 as shown in FIG. 1, the brace itself will generally conform to the joint at the wearer's knee 31. Also as clearly shown in FIG. 1, the longitudinal side binding or seam 21 of the brace 10 which joins the one piece blank's two side edges 14, 15 is positioned generally parallel to the brace's curved longitudinal axis 22. And very importantly relative to this invention, the transverse seams or bindings 16c, 17c which close each of the elongated slits 16, 17 in the brace's blank 11 are positioned above and below, respectively, the primary fold line 32 of the wearer's skin on the skin surface area 33 to the rear of the wearer's knee. These transverse binding lines 16c, 17c extend around the back skin surface area 33 of the wearer's leg to end points 23, 24, 25 and 26 located approximately midway on the opposed side faces 34 of the wearer's leg 30, compare FIGS. 1 and 2. In other words, neither transverse binding line 16c or 17c overlies, nor is operably enough close to, the fold line 32 of the wearer's skin at the rear skin surface area 33 of the wearer's knee 31 so as to cause irritation at that skin fold line during active exercise by the brace's wearer. In this regard, and as shown in FIG. 3, the transverse binding lines 16c, 17c are generally parallel one to the other and, therefor, also generally parallel to the fold line 32 of the wearer's skin on the rear skin surface of the wearer's knee, when the brace is being worn.

The one piece elastic brace 10 of this invention, as well as the method by which it is constructed, provides a unitary elastic brace that retains body heat to warm the knee or elbow joint and that tends to increase blood circulation. Further, the brace 10 provides a multi-directional stretch brace that provides compression and support to the knee or elbow joint during active exercise by the wearer. And this combination of heat retention and compression reduces the chance of strain or injury to the knee or elbow joint during active exercise. Also, and when the brace 10 is formed from the preferred rubber foam laminate beforementioned, same tends to cushion the knee or elbow joint against blows and bumps to that joint during use by the wearer, and this protection is not significantly reduced when the brace becomes wet with sweat because the rubber foam laminate is not adversely affected due to water absorption. And importantly relative to this invention, and because of the two spaced transverse stitching or binding lines 16c, 17c of this brace 10 structure, as well as the method by which the brace is fabricated, those binding lines or seams do not irritate the rear skin surface of the wearer's knee, or the inner skin surface of a wearer's elbow, during heavy exercise.

Figure 5:
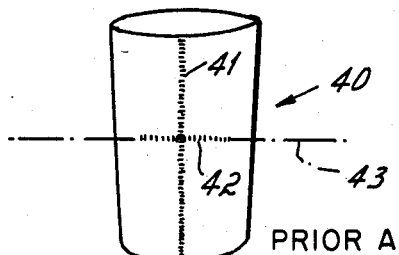
FIG. 5 is a rear view of a knee brace in accord with one example of the prior art.
Figure 6:
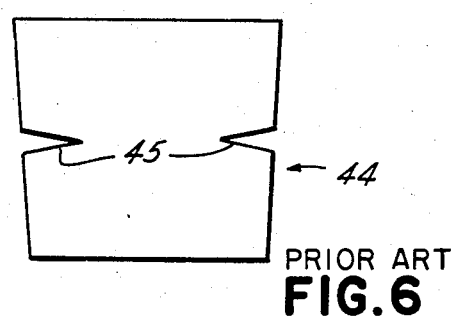
FIG. 6 is a top view of the blank from which the FIG. 5 knee brace is fabricated.

One prior art knee brace 40 over which this invention constitutes an improvement is shown in FIGS. 5 and 6. The FIG. 5 tubular knee brace 40 includes a longitudinal seam 41 that runs down the rear skin surface of the wearer's leg, and a transverse seam 42 that runs across the rear skin surface of the wearer's leg exactly at the fold line 43 of the skin surface in back of the wearer's knee. This knee brace is fabricated from a blank 44 shown in FIG. 6 that includes two darts 45 cut out from opposite side edges of that blank. Obviously this brace provides the exact problem over which applicant's invention overcomes, namely, a single transverse seam 42 that is substantially co-extensive with the fold line 43 of the wearer's skin surface at the back of the wearer's knee when the knee brace is being worn.

Figure 7:
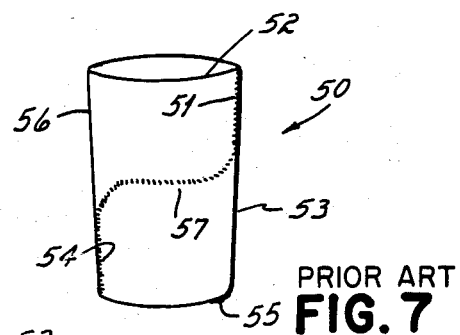
FIG. 7 is a rear view of a knee brace in accord with another example of the prior art.
Figure 8:
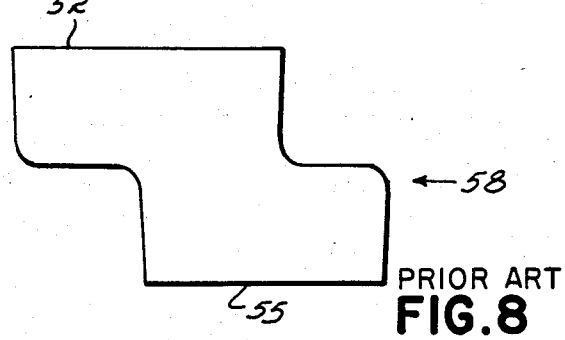
FIG. 8 is a top view of the blank from which the FIG. 7 knee brace is fabricated.

A second prior art knee brace 50 embodiment, with the same disadvantages as the first prior art embodiment, is illustrated in FIGS. 7 and 8. The knee brace 50 includes a first longitudinal seam line 51 that extends halfway down from the top edge 52 of the knee brace on one side 53, and a second longitudinal seam line 54 that extends halfway up from the bottom edge 55 of the knee brace on the other side 56. These longitudinal seam lines 51, 54 are joined by a transverse seam line 57 that is located midway between the top 52 and bottom 55 edges of the brace. The blank 58 configuration for the knee brace 50, prior to being sewn into the tubular sleeve brace configuration, is shown in FIG. 8. As noted, this second prior art knee brace embodiment shown in FIGS. 7 and 8 has the same disadvantage as the first prior art embodiment, namely, the existence of a binding or seam line 57 that overlies the fold line of a wearer's skin on the rear skin surface of a wearer's knee when the brace is being worn.

Having described in detail the preferred embodiment of my invention, what I desire to claim and protect by Letters Patent is:

1. A brace for knee or elbow comprising
    a sleeve of elastic material that is of generally tubular configuration, said sleeve having a curved configuration when it is viewed from the side and when not being worn, and
    upper and lower transverse seam lines spaced one from the other on the inside surface of said sleeve, said seam lines closing elongated eye shaped openings in said sleeve which openings were cut out initially in order to provide the curved configuration, the spacing of said seam lines insuring that neither seam line overlies the fold line of the wearer's skin surface when the brace is being worn, thereby minimizing irritation of the wearer's skin at that skin fold line.

2. A brace as set forth in claim 1, said transverse seam lines being generally parallel one to the other.

3. A brace as set forth in claim 2, said transverse seam lines each having a length approximately equal to one-half the circumferential peripheral length of said sleeve.

4. A brace as set forth in claim 2, said transverse seam lines being spaced one from the other so that the distance between said upper and lower seam lines, the distance between said upper seam line and said brace's upper edge, and the distance between said brace's lower seam line and said brace's lower edge are all approximately equal.

5. A brace as set forth in claim 4, said sleeve being formed from a blank in which said elongated eye-shaped openings extend out to one edge of said blank, and including
   a longitudinal seam line that joins the opposed side edges of said blank to construct said sleeve.

6. A method of constructing a tubular brace particularly adapted for use on a wearer's knee or a wearer's elbow, said method comprising the steps of
   providing a one-piece brace blank having top, bottom and opposed side edges, said blank incorporating two elongated eye shaped openings that are generally parallel to said blank's top and bottom edges, said openings subdividing that blank section within which same are located into three subsections of substantially equal height,
   binding the top and bottom edges of each of said slits together to establish two substantially transverse seam lines, and
   binding the side edges of said blank together, thereby providing a tubular brace with transverse seam lines that do not overlie the fold line of a wearer's skin when the brace is worn on either a knee joint or an elbow joint.

7. A method as set forth in claim 6, said transverse seam lines being generally parallel one to the other.

8. A method as set forth in claim 7, said transverse seam lines each having a length approximately equal to one-half length of said blank.

9. A method as set forth in claim 7, said transverse seam lines being spaced one from the other so that the distance between said upper and lower seam lines, the distance between said upper seam line and said brace's upper edge, and the distance between said brace's lower seam line and said brace's lower edge are all approximately equal.

10. A method as set forth in claim 9, said elongated eye shaped openings extending out to one edge of said blank.

* * * * *